United States Patent [19]

Berglund

[11] 4,425,119
[45] Jan. 10, 1984

[54] IMPLANTABLE DEVICE FOR INTRAVASCULAR ACCESS

[76] Inventor: Rickey T. Berglund, 2275-68 Caminito Pescado, San Diego, Calif. 92107

[21] Appl. No.: 342,113

[22] Filed: Jan. 25, 1982

[51] Int. Cl.³ .............................................. A61M 5/00
[52] U.S. Cl. ..................................... 604/175; 128/1 R
[58] Field of Search ............. 604/4, 27, 29, 30, 32–34, 604/43, 52, 53, 93, 167, 169, 175, 178, 237, 284, 891, 896; 128/1 R; 3/1

[56] References Cited

U.S. PATENT DOCUMENTS

| | | | |
|---|---|---|---|
| 2,065,779 | 12/1936 | Williams | 604/178 |
| 3,461,869 | 8/1969 | Hargest | 604/175 |
| 3,540,451 | 11/1970 | Zeman | 604/175 X |
| 3,663,965 | 5/1972 | Lee, Jr. et al. | 604/175 X |
| 3,765,032 | 10/1973 | Palma | 604/175 X |
| 3,783,868 | 1/1974 | Bokros | 604/891 |
| 3,919,724 | 11/1975 | Sanders et al. | 604/175 X |
| 3,991,756 | 11/1976 | Synder | 604/175 X |
| 4,015,601 | 4/1977 | Bokros et al. | 604/175 |
| 4,016,884 | 4/1977 | Kwan-Gett | 604/175 |
| 4,069,826 | 1/1978 | Sessions et al. | 604/178 |
| 4,084,606 | 4/1978 | Mittleman | 604/30 X |
| 4,092,983 | 6/1978 | Slivenko | 604/175 |
| 4,106,491 | 8/1978 | Guerra | 604/167 |
| 4,108,173 | 8/1978 | Slivenko et al. | 604/175 |
| 4,108,174 | 8/1978 | Slivenko | 604/175 |
| 4,164,221 | 8/1979 | Bentley et al. | 604/52 |
| 4,183,357 | 1/1980 | Bentley et al. | 604/175 |
| 4,248,224 | 2/1981 | Jones | 604/53 |
| 4,306,545 | 12/1981 | Ivan et al. | 604/175 X |
| 4,318,401 | 3/1982 | Zimmerman | 604/53 X |
| 4,321,914 | 3/1982 | Begovac et al. | 604/896 X |
| 4,349,021 | 9/1982 | Raible | 604/175 |
| 4,350,157 | 9/1982 | Hoffa | 128/1 R X |

Primary Examiner—C. Fred Rosenbaum
Assistant Examiner—Michelle N. Lester
Attorney, Agent, or Firm—Gordon L. Peterson

[57] ABSTRACT

An implantable device for providing extracorporeal access to a blood vessel includes a core section having an axial passage for communication between the blood vessel and the exterior of an organism's skin. The core section is seated within a housing having a lower portion in the form of a tubular band which encompasses the blood vessel. The upper part of the housing has a circular rim supported by spaced-apart struts, forming an open-sided, bowl-like structure, through the center of which the upper portion of the core protrudes. The bowl-like structure allows the incised edges of the skin around the access site to be tucked into its interior. A sealing member is threaded onto the protruding section of the core and is configured to hold the skin so that the subcutaneous tissue can grow between the struts and reattach itself to the skin, thereby resulting in a permanent and stable implant. The interface between the core passage and the blood vessel is sealed by a resilient valving member which has a peripheral wall with one or more slits. The valve is opened by axial distension, so that the slits are opened to provide ports in communication with the interior of the blood vessel. To actuate the valve, a cannula having a movable rod is inserted into the passage, and the rod is urged downwardly so that its tip axially distends the valving member.

21 Claims, 8 Drawing Figures

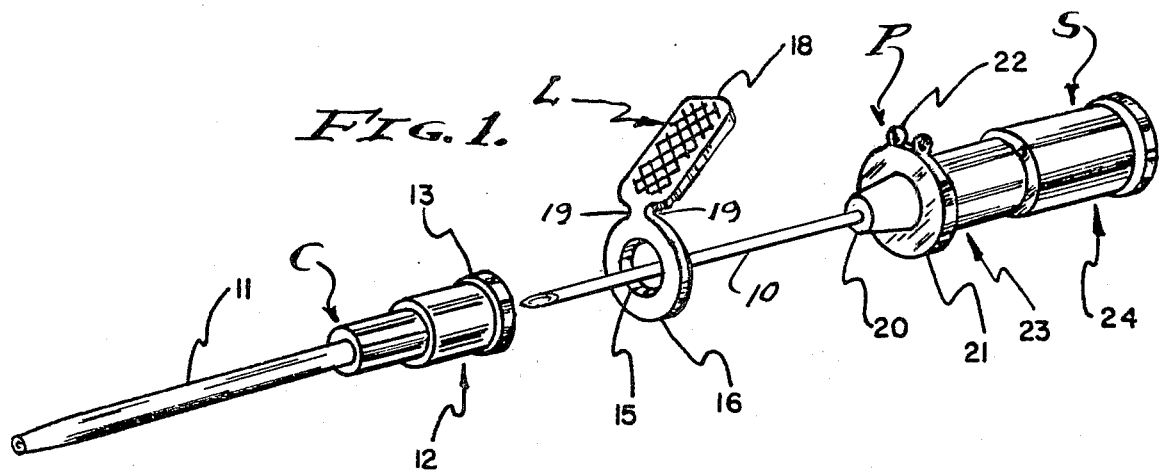
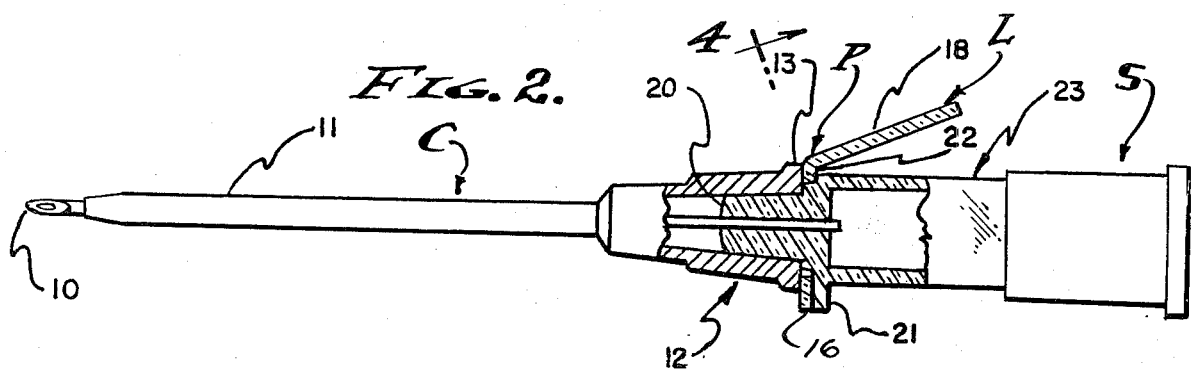
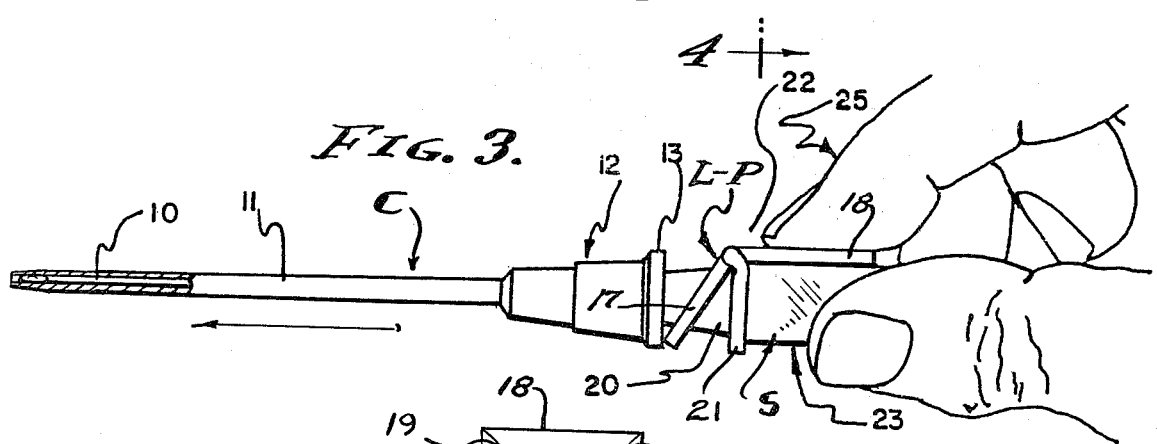
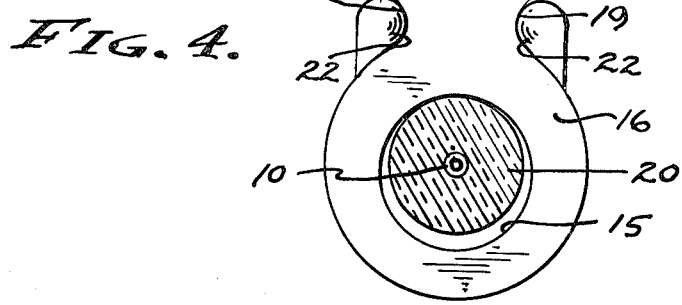

IMPLANTABLE DEVICE FOR INTRAVASCULAR ACCESS

BACKGROUND OF THE INVENTION

The present invention relates generally to the field of providing long term extracorporeal access to the circulatory system of a living organism. In particular, it relates to a device which is permanently implantable in the skin of an organism, and which provides a more or less permanent means of access to the organism's circulatory system.

A number of medical procedures require repeated access to a patient's vascular system. In such procedures as hemodialysis and plasmapheresis, for example, it is necessary to tap into a patient's vascular system, withdraw relatively large quantities of blood therefrom, and return the blood to the system. Frequently, in the past, it has been the practice to withdraw blood by means of a needle inserted into one blood vessel, and to return the blood by means of a needle inserted into another blood vessel. However, the treatment of many patients requires repeated withdrawals of blood over a prolonged period of time. It was found that repeated insertions of needles into the veins and arteries resulted in substantial trauma to these blood vessels. Aside from the possibility of tissue damage, there is the pain and discomfort associated with the insertion of the needles.

Thus, over the years, various devices have been developed for the purpose of providing a permanent or semi-permanent means of extracorporeal access to a blood vessel. The most common approach taken by the prior art is to provide a device which is implanted in the tissues of an organism and which provides communication between a blood vessel and the exterior of the organism's body. Typically, such devices are provided with valving means to provide, selectively, extracorporeal access to the blood vessel.

One type of implantable blood vessel access device is disclosed in U.S. Pat. No. 3,765,032 to Palma. In devices of this type, a section of a blood vessel is removed and replaced with a tube having one end in communication with a blood vessel and another end projecting through the skin. The projecting end has a valve for selectively blocking and passing blood from the blood vessel. One drawback to such devices is that their removal requires a vascular graft to replace the previously removed portion of the blood vessel. In addition, the hardware required for implanting such devices is relatively complex, and in such devices, the blood is exposed to a substantial amount of foreign material in the form of the tubing, thereby increasing the probability of thrombosis.

Another type of implantable device is disclosed in U.S. Pat. No. 3,991,756 to Snyder. In devices of this nature, a cannula is surgically implanted adjacent to a blood vessel and interfaces therewith along a longitudinal wall. One end of the cannula protrudes through the skin, and this protruding end has a sealable opening. The wall of the cannula is provided with several access openings which allow a needle inserted into the cannula to puncture the blood vessel at selected sites. While devices of this type eliminate the problems associated with repeated puncturing of the skin, they do not totally eliminate the trauma associated with repeated puncturing of the blood vessel wall.

Still another type of vascular access device which has recently been developed is illustrated in U.S. Pat. No. 4,015,601 to Bokros, et al; U.S. Pat. No. 4,092,983 to Slivenko; and U.S. Pat. No. 4,108,173 to Slivenko et al. In devices of this type, a tubular conduit is inserted into a blood vessel. The conduit is in communication with a housing which extends through the patient's skin. The conduit has an aperture which communicates with the housing, and the housing has a valving mechanism including a movable valve body with a port which is alignable with the aperture. The valve body is movable between positions of alignment and non-alignment of the aperture and the port selectively to allow access to the blood vessel from the exterior of the organism. While devices of this type are capable of providing satisfactory vascular access and sealing of the access point from contamination, the valving mechanism associated with these devices is relatively bulky and complex. Moreover, installation of the conduit by which these devices communicate with the blood vessel requires a substantial interruption of the blood vessel, and there is a great deal of structure which thus invades the interior of the blood vessel, with a resulting increase in the likelihood of thrombosis.

A more recent development in the art of blood vessel access devices is illustrated in U.S. Pat. No. 4,164,221 to Bentley et al. In devices of this type, a passageway is implanted through the skin of the patient and has one end communicating with the blood vessel wall. The other end of the passageway protrudes through the skin and is closed by means of a threaded cap. The passageway is sealed by means of a plug which can be removed and inserted by means of an attachable stem. While this approach allows a minimum invasion of the interior of the blood vessel, devices of this type necessitate a significant amount of above-skin structure which is both unsightly and uncomfortable. Moreover, the insertion and removal of the plug into and out of the passageway creates a force perpendicular to the blood vessel wall, and these forces can result in undesirable stresses being created at the site where the passageway adjoins the vessel wall and is sutured thereto. Thus, care must be taken not to insert or remove the plug before the suture site is well healed, and subsequently, insertion and removal of the plug must be done gently and carefully.

From the foregoing, it can be appreciated that there are a number of objectives which the prior art has attempted to meet in the design of intravascular access devices. For example, an important criterion has been the minimization of bulky hardware, and especially to minimize the amount of structure which invades the blood vessel. A related objective is to allow installation, and possibly removal, of the device with minimum damage to the vessel and the surrounding tissues. Moreover, it is necessary that such devices allow repeated use over prolonged periods of time without substantial trauma to the blood vessel, and that when not is use, such devices provide effective sealing of the blood vessel and the access site from the external environment. Finally, it is necessary that such devices be adapted for prolonged periods of implantation and so must be adapted to minimize discomfort to the patient.

From the foregoing discussion it can be appreciated that, while the prior art devices meet some of the foregoing objectives, none of the prior art devices discussed above meets all of these objectives.

SUMMARY OF THE INVENTION

Broadly described, the present invention is an implantable device for accessing a blood vessel, particularly an artery. The device comprises a central core section adapted to communicate between an aperture formed in a blood vessel and the exterior surface of the patient's skin. The core section terminates in a peripheral flange which seats against the interior wall of the blood vessel and which forms a valve seat for an elastomeric valving member. The valving member, in its normally closed position, seats against the valve seat flange and closes the passage in the core from communication with the blood vessel interior through the blood vessel aperture. Surrounding the core is a housing having a lower portion in the form of an axially divided tubular band, the divided sections of which are adapted to be placed around the exterior surface of the blood vessel wall to provide support for the blood vessel against the radial forces imposed by the actuation of the valving member. The upper portion of the housing forms a bowl-like structure which underlies the skin surrounding the opening therein through which the core section passes, and which provides a seat for a frustoconical seal which surrounds the core section. The skin surrounding the skin opening is captured between the exterior surface of the seal and the interior surface of the bowl-like structure so that the skin is sealed therebetween. An in-growth ring at the base of the frustoconical seal allows the skin around the opening to bond itself to the housing, thereby effecting a completed seal between the skin and the structure of the implanted unit and isolating the sub-cutaneous tissues from the external environment except through the passage through the core section.

Sealing of the passage is provided by a removable plug having a ribbed shaft which snugly fits into the passage. The shaft is saturated with a sterile, antibacterial, blood-compatible solution to complete the isolation of the blood vessel interior from the exterior environment and to prevent infection.

The vascular access device of the present invention is designed preferentially for use in conjunction with a unique valve actuating device which also provides access to the interior of the blood vessel for simultaneous inflow of fluid thereto and outflow of fluid therefrom. This valve actuation device is in the form of a dual-channel cannula which sealingly fits the interior of the core passageway when the aforementioned plug is removed. Extending axially through the center of the cannula is a rod actuated by a plunger. When the plunger is depressed, the distal tip of the rod is urged against the interior of the elastomeric valving element, urging the latter away from its seat by axial distension. This distension spreads open a pair of slits in the circumferential wall of the valving element so that the slits become access ports which are in fluid communication with the interior of the blood vessel. The interior of the blood vessel is now in communication with the cannula, thereby allowing fluid flow between the blood vessel and one or more exterior conduits via the channels of the cannula.

From the foregoing, and from the detailed description which follows, it will be seen that the present invention overcomes the aforementioned limitations of the prior art by providing a mechanism which, at once, allows convenient access to the interior of a blood vessel by means of a relatively simple structure which is easily implanted with minimum trauma to the vessel and the surrounding tissues. Moreover, the present invention provides ample support for the blood vessel and the surrounding tissue so that repeated use over extended periods of time is provided with both reliability and a minimum of discomfort and tissue damage. In addition, it can be seen that effective sealing of the subcutaneous tissues, including the blood vessel, is provided so as to minimize the possibility of contamination by dirt and microorganisms. Finally, it will be appreciated that the present invention provides a structure which presents a minimal invasion of the interior of the blood vessel, thereby minimizing blood flow obstruction and the resultant possibility of thrombus formation.

BRIEF DESCRIPTION OF THE DRAWINGS

FIG. 1 is a perspective view of the preferred embodiment of an intravascular access device, in accordance with the present invention, in its implanted position;

FIG. 2 is an elevational view, partially in section, showing the intravascular access device as it appears during an intermediate stage of the implantation procedure;

FIG. 3 is an elevational view, partially in section, showing the implanted intravascular access device with its associated sealing plug;

FIG. 4 is a cross-sectional view of the implanted intravascular access device of the present invention in conjunction with its associated valve actuation device, showing the valving element of the access device in its closed position;

FIG. 5 is a cross-sectional view along line 5—5 of FIG. 4;

FIG. 6 is a cross-sectional view along line 6—6 of FIG. 4;

FIG. 7 is a cross-sectional view, similar to that shown in FIG. 4, showing the valving element in its open position; and FIG. 8 is a cross-sectional view along line 8—8 of FIG. 7.

DETAILED DESCRIPTION OF THE INVENTION

FIGS. 1, 2, and 3 illustrate a preferred embodiment of an intravascular access device 10 in accordance with the present invention. The device 10 comprises an external housing 12 adapted for implantation in the tissues of a living organism, hereinafter referred to as the "patient". The housing 12 is made of a biologically compatible material, preferably a somewhat resilient plastic. As shown, the lower portion of the housing comprises a tubular band 14, the bottom of which is axially divided so as to form a pair of radially separable segments 14a and 14b (FIG. 2). The band 14 provides structural support for an accessed blood vessel 16 in a manner which will be described later on. The upper portion of the housing 12 comprises a plurality of outwardly flared strut elements 18 supporting a substantially circular rim 20. The struts 18 and the rim 20 form a bowl-like structure which contributes to the sealing of the patient's skin 22 into and around the device 10, as will be more fully described hereinafter.

The housing 12 has an axial bore 23 therethrough into which is snugly seated a vertical tubular core section 24, made of a biologically compatible material, preferably a plastic. The core 24, which extends upwardly into the bowl structure formed by the struts 18 and rim 20, has an upper end 26 which is substantially coplanar with the rim 20, and a lower end terminating in an annular flange 28. The flange 28 may be integral with the core 24, or, preferably, it may be a separate unit, formed of a more resilient material which is adhesively attached to the core 24. The upper terminus 26 and the lower terminus 28 are joined by an axial passage 30. The passage 30 is sealed at its lower end by a biologically compatible, elastomeric valving member 32, which, in its normally closed position, seats against the flange 28. The valving member 32, which may, for example, be made of latex, will be described more fully hereinafter.

The bowl structure formed by the struts 18 and rim 20 defines a flat annular surface 34 at the bottom thereof, where the core section 24 protrudes from the housing 12. This annular surface 34 provides a seat for a substantially annular ingrowth base 36, which is of a material, such as pyrolitic carbon, to which living tissue is capable of bonding, for purposes which will be explained more fully later on. Similarly, the outer perimeter of the core section 24 just above the flange 28 is indented to define an annular groove which provides a seat for an ingrowth ring 38 of a similar ingrowth-promoting material.

Referring now particularly to FIG. 2, the implant device 10 is illustrated just after positioning at the access site. The access site has been prepared by forming an incision which exposes a suitable length of the blood vessel 16, and which allows access to the entire circumference of the blood vessel along this length. A circular opening is cut into the upper surface of the blood vessel wall so as to allow passage of the core section 24 therethrough, thereby allowing the capture of the blood vessel wall between the flange 28 and the interior surface of the central portion of the housing 12, which is appropriately curved to conform to the outer surface of the blood vessel wall. The sections 14a and 14b of the tubular band 14, which have been previously separated so as to allow passage over the blood vessel 16, are now urged together, as indicated by the arrows 40 in FIG. 2, to form the completed tubular band 14, as shown most clearly in FIG. 3. In its closed position, the band 14 completely encircles the blood vessel 16 and provides positional stability for the implant device 10 with respect to the blood vessel 16, while also providing a load-bearing structure which spreads the load on the vessel imposed by the radial stresses due to the actuation of the valving member 32, as will be more fully described hereinafter. During this stage in the implanting process, positional stability between the core 24 and the housing 12 is provided by the mating of an annular bead 42 on the interior surface of the housing 12 with an annular groove 44 on the exterior surface of the core section 24 just above the site of the ingrowth ring 38.

Referring now to FIG. 3, the final step of the implantation process is illustrated. The edges of the patient's skin 22 surrounding the incision therein are tucked into the bowl structure 18, 20, so that the incised edges of the skin comes into intimate contact with the upper surface of the ingrowth base 36. The skin 22 thus forms a frustoconical tuck 46 which is in intimate contact also with the struts 18 and rim 20 of the bowl structure formed by these elements. It has been determined that the bowl structure should be formed so that the tuck 46 is formed at an angle of approximately 30 degrees from the vertical, although this angle is not critical. Finally, a frustoconical wedging seal 48 of a suitable biologically compatible material, having an internally threaded axial bore 49 therethrough, is threaded onto the exposed section of the core 24 which bears external threads 50. This threading may be accomplished by a suitable tool (not shown) which is engageable with one or more slots or bores 51 (one of which is shown in FIGS. 4 and 7) in the upper surface of the wedging seal 48. When the wedging seal 48 is thus threaded, its sloped peripheral surface 52, which conforms to the skin tuck 46, seals and locks the skin tuck 46 in place in the bowl-like structure 18, 20.

The wedging seal 48 provides at least three very important functions. First, by snugly fitting between the skin tuck 46 and the external surface of the core section 24, the wedging seal 48 seals and isolates the underlying tissue at the access site from the external environment. Second, the wedging seal 48 maintains the incised edge of the skin tuck 46 and the surface of the ingrowth base 36 in intimate contact with each other, so as to promote the healing of the skin tuck and the attachment thereto to the ingrowth base 36. Third, as the wedging seal 48 is threaded onto the core section 24, the bottom of the wedging seal comes into contact with the surface of the ingrowth base 36. Thus, continued tightening of the wedging seal 48 onto the core 24 produces an upward vertical force on the core 24, with the result that the inner surface of the flange 28 is urged firmly against the adjacent vascular wall surface, thereby creating an effective seal therebetween. It can thus be seen that tightening of the wedging seal 48 onto the core 24 not only locks the core 24 and the housing 12 to each other to form a stable unitary structure, but also creates a secure, fluid-tight seal between the core, the housing and the blood vessel. The result is a firm, secure, fluid-tight implant, with components of the implanted device cooperating with the skin and the blood vessel to form a stable structure. To this end, it should be noted that the implant device 10 is further stabilized and made secure in the implant site by the ingrowth of subcutaneous tissue 52 through the spaces between the struts 18 so as to heal to the underside of the skin tuck 46, as shown in FIG. 2.

The sealing contact between the inner surface of the flange 28 and the adjacent surface of the wall of the blood vessel 16 produced by the mechanical interaction between the wedging seal 48, the core 24, and the housing 12, has several advantageous aspects. First, as previously discussed, a fluid-tight seal is created between the vessel wall and the flange 28. Second, structural support is added to the vessel wall so as to enhance the vessel's ability to withstand the stresses of valve actuation, as will be subsequently discussed. Third, the sealing engagement provides a maximum unobstructed flow passage through the vessel by minimizing the invasion of the vessel interior by the flange 28 and the valving element 32. Finally, the intimate fit between the flange 28 and the blood vessel wall substantially eliminates areas in which blood could stagnate, with the resultant likelihood of thrombus formation.

The structural stability of the device, as well as its sealing integrity, is enhanced by the healing of the edges of the blood vessel wall around the access aperture formed therein to the ingrowth ring 38. This bonding of the blood vessel tissue to the ingrowth ring 38 enhances the seal formed between the flange 28 and the blood vessel wall, as well as the sealing contact between the exterior surface of the blood vessel wall and the housing 12. Moreover, the structure of the vessel is further strengthened to withstand the stresses of valve actuation.

Again referring to FIG. 3, a plug or cap 54 is provided for sealing the upper or exterior opening of the passage 30 through the core section 24. The plug 54, which is preferably made of a somewhat resilient, biologically compatible plastic, comprises a shaft 56 having a tapered end 58 and a plurality of annular ribs 60. The maximum diameter of the ribs 60 is preferably approximately equal to, or slightly greater than, the inside diameter of the passage 30, so that the insertion of the shaft 56 effects an essentially airtight and fluid-tight sealing of the passage. The material of the shaft 56 can advantageously be made somewhat porous and saturated with a sterile, antibacterial, blood compatible saline solution, so as to enhance further the antibacterial seal provided by the plug 54. The upper end of the shaft 56 terminates in a domed head 62, which is preferably made in a flesh-tone color so as to minimize the visibility of the access site in the patient's skin. As shown in FIG. 3, when the plug 54 is fully inserted into the passage 30, the flat underside of the domed head 62 is seated against the adjacent surface of the wedging seal 48. To enhance the seal created between the plug 54 and the wedging seal 48, the underside of the domed head 62 may be coated with a suitable adhesive.

The internal structure of the core section 24 and of the valving member 32 is illustrated in FIGS. 4, 6, and 7. As previously noted, the valving member 32 is located in the lower or interior end of the passage 30. Seated in the passage just above the valving member 32 is cannula support member 64 having a tapered seating surface 66 at its upper end. Just below the seating surface 66, an apertured cross member 68 diametrically traverses the interior of the cannula support member 64.

The peripheral wall of the resilient valving member 32 is provided with a pair of diametrically-opposed horizontal slits 70, only one of which is shown in FIG. 4. These slits 70 provide the valve ports, in a manner to be described later on. As can be seen from FIG. 4, the lower portion of the cannula support member 64 and the interior of the resilient valving member 32 defines a substantially cylindrical chamber 72, the volume of which should be no more than approximately 1 cubic centimeter, for purposes which will later be explained. The underside of the valving member 32, forming the lower surface of the chamber 72, is preferably provided with a small central notch or dimple 74, the purpose of which will also be subsequently explained.

The intravascular access device 10 of the present invention is designed preferentially for use with a valve actuation cannula 100 as best shown in FIGS. 4 through 7. The cannula 100 comprises a vertical shaft 102 having an axial bore 104 therethrough, said axial bore being divided by a vertical partition 106 into a pair of adjacent parallel channels 108a and 108b. See FIG. 6. As also shown in FIG. 6, the partition 106 has an enlarged hollow central portion 110 which forms a guideway for a valve-actuation rod 112. The shaft 102 has an open end defined by a tapered peripheral wall section 114, which seats against the cannula seating surface 66 of the cannula support member 64 when the shaft 102 is inserted into the passage 30 in the core section 24. Part way up the exterior wall surface of the shaft 102 is a locking rib 116 which mates with a locking groove 118 in the passage 30 (FIG. 2) when the shaft 102 is rotated in the passage 30, thereby locking the shaft 102 into the passage 30 in such a manner that the tapered wall section 114 of the shaft seats snugly against the cannula seating surface 66 as shown. It may be advantageous to provide a second inwardly tapered section 120 in the peripheral wall of the shaft 102 just above the locking rib 116 so as to provide a seating interface with an inwardly tapered surface 122 near the top of the passage 30 (FIG. 2).

The top of the axial bore 104 terminates in a radial bore 124, which is divided into a pair of adjacent parallel channels 126a and 126b (FIG. 5) by a partition (not shown). The radial bore 124 extends into an outwardly tapered fitting 128, adapted for connection with a pair of tubes 130a and 130b which provide fluid communication with a fluid pump (not shown) and blood treatment apparatus (not shown).

The valve actuation rod 112 is, itself, actuated by means of a thumb press button 132, situated at the top or proximal end of the rod 112. Situated on the rod 112 just below the thumb press button 132 is a pair of diametrically-opposed angular extensions 134. The rod 112 emerges from the top of the shaft 102 through an annular chamber 136 which communicates with the exterior of the shaft 102 through a slot 138. When it is desired to open the valve 32, the shaft 102 is rotated so that the extensions 134 are aligned with the slot 138, and the shaft is then urged downwardly by means of pressure on the thumb press button 132, until the extensions 134 are contained within the annular chamber 136. The shaft is then locked into this position by a 90° rotation of the shaft 102, which brings the extensions 134 out of alignment with the slot 138, so that the upper surfaces of the extensions 134 abut against the upper wall of the chamber 136. When it is desired to release the shaft 102 and move it upwardly so as to close the valve 32, unlocking of the shaft is accomplished by simply reversing the steps of the locking process. As shown in FIGS. 4 and 7, a pair of finger grips 140 may be provided at the top of the shaft 102 to facilitate these operations.

The operation of the valving member 32 by means of the valve actuation cannula 100 is illustrated in FIGS. 7 and 8. As best shown in FIG. 7, the shaft 102 is urged downwardly and locked in its extreme downward position in the manner previously described. In this position, the distal or lower tip of the rod 112 engages the dimple 74 on the inner surface of the resilient valving member 32, and thereby axially distends the peripheral wall of the resilient valving member 32. This axial distension causes the lips of the slits 70 to part, thereby providing a pair of ports 70a and 70b, which open below the flange 28 into the interior of the blood vessel 16, as best shown in FIG. 8. From FIG. 8, it can be seen that the ports 70a and 70b allow communication between the interior of the blood vessel 16 and the cannula channels 108a and 108b respectively, such communication being by way of the chamber 72 formed between the valving member 32 and the cannula support member 64.

Thus, when the valve member 32 is actuated, and the ports 70a and 70b are open, a negative pressure can be applied to the conduit 130a to draw blood out of the blood vesssel 16, into the port 70a through the cannula channels 108a and 126a and out into the conduit 130a, from which the blood can be directed to the treatment apparatus. The blood can then be returned to the blood vessel by means of the conduit 130b, the cannula channels 126b and 108b, and the port 70b. This fluid motion is indicated by arrows 142a and 142b in FIG. 8. To be sure, some mixture of the outgoing and incoming blood flows will occur in the chamber 72. However, since, as previously noted, the volume of the chamber 72 is relatively small, the degree of mixing of treated and untreated blood is quite minimal with respect to the overall volumes involved.

When the treatment procedure is finished, the shaft 102 is unlocked and withdrawn, in the manner previously described, and the natural resiliency of the valving member 32 returns it to its original position, as shown in FIG. 4, in which it rests against the seating flange 28, and in which the peripheral slits 70 are closed. The cannula 100 is then removed from the passage 30 by twisting the locking rib 116 out of its mating groove 118. The cannula is then simply lifted out of the passage which is then resealed by replacement of the cap or plug 54.

It will be appreciated from the foregoing description that the actuation of the valving member 32 will produce a radial stress on the wall of the blood vessel 16. As previously noted, this stress is distributed around the entire circumference of the blood vessel wall by the tubular band 14, while the flange 28 and ingrowth ring 38 help strengthen the vessel wall at the access site so as to better withstand these stresses.

While the valve actuation cannula described above has been described as being of a dual channel nature for simultaneous flow out of and into the blood vessel, it should be noted that a single channel cannula can be used if flow in only one direction is needed.

There has thus been described an intravascular access device which is adapted for relatively simple, and yet highly secure, implantation. It can further be seen that this implantation is accomplished with minimum damage to the blood vessel involved, and with minimum trauma to the surrounding tissue. Furthermore, the valving mechanism of the device not only provides high integrity sealing of the access site, but also allows repeated valve actuation over extended periods of time with minimal risk of damage to the blood vessel or other tissues and with minimum discomfort to the patient. Moreover, the structure of the device presents only a minimal obstruction of the blood vessel interior. All of the goals are accomplished with relatively simple, compact hardware which is adapted to be relatively unobtrusive, in a visual sense.

What is claimed is:

1. A device for providing access to a blood vessel of a living organism through the skin of said organism, comprising:
a core section having a first terminus adapted for insertion through an aperture in the wall of a selected blood vessel, a second terminus adapted for protrusion through an incision in said skin, and passage means extending between said termini;
first attachment means for attaching said core section to said blood vessel;
second attachment means for attaching said core section to said skin and to tissues underlying said skin;
valving means, in said passage means, adapted for axial movement between a first position which seals said passage means and a second position which allows fluid communication between said passage means and the interior of said blood vessel when said first terminus is inserted into said blood vessel;
load-distributing means connected to said core section and adapted to at least partially encircle the blood vessel to distribute stresses suffered by said blood vessel as a result of the movement of said valving means;
means for selectively sealing said passage means from the second terminus;
housing means, having an axial bore for receiving said core section;
said second attachment means including a first part of said housing means, and said load-distributing means including a second part of said housing means;
said second attachment means including means for forming and receiving a tuck of skin from around the edges of said incision and means for maintaining sid tuck of skin in said means for forming and receiving; and
said first attachment means including peripheral flange means on said core section proximate said first terminus for (a) providing a seat for said valving means, and (b) engaging the interior wall of said blood vessel.

2. The device of claim 1, wherein said means for forming and receiving includes means for permitting tissues underlying said skin to reattach to said tuck of skin through said means for forming and receiving.

3. The device of claim 2, wherein said means for forming and receiving comprises a substantially annular rim member supported by a plurality of spaced-apart strut members to form a substantially open-sided structure.

4. The device of claim 3, wherein a portion of said core section extends axially into said structure, and wherein said means for maintaining said tuck of skin comprises:
a sealing member having an axial bore;
means in said bore engageable with said axially-extending portion of said core section; and
a peripheral surface on said sealing member adapted for providing a sealing contact with said tuck of skin.

5. The device of claim 4, wherein said structure is adapted to form and receive a substantially frustoconical tuck of skin, and said sealing member has a mating frustoconical configuration.

6. The device of claim 1 wherein said means for maintaining said tuck of skin is engageable with said core section and wherein said core section has limited axial movement within said housing means to urge said flange means against the interior wall of said blood vessel.

7. The device of claim 1 wherein said second attachment means further comprises:
means for promoting an ingrowth bonding thereto of said tuck of skin.

8. The device of claim 5 wherein said first attachment means further comprises:
a substantially annular band of tissue ingrowth-prmoting material on said passage means, so located as to allow the bonding thereto of blood vessel tissue surrounding said aperture in said blood vessel wall.

9. A device for providing access to a blood vessel of a living organism through the skin of said organism, comprising:
a core section having a first terminus adapted for insertion through an aperture in the wall of a selected blood vessel, a second terminus adapted for protrusion through an incision in said skin, and passage means extending between said termini;
first attachment means for attaching said core section to said blood vessel;
second attachment means for attaching said core section to said skin and to tissues underlying said skin;
valving means, in said passage means, adapted for axial movement between a first position which seals said passage means and a second position which allows fluid communication between said passage means and the interior of said blood vessel when said first terminus is inserted into said blood vessel;

load-distributing means connected to said core section and adapted to at least partially encircle the blood vessel to distribute stresses suffered by said blood vessel as a result of the movement of said valving means;

means for selectively sealing said passage means from the second terminus; and said lead distributing means including a tubular member shaped and dimensioned substantially to encompass and to engage said blood vessel.

10. The device of claim 11 wherein said valving means comprises:

a peripheral wall adapted for axial distension from said first position to said second position and for resilient return from said second position to said first position; and means in said peripheral wall for allowing fluid communication through said passage means when said peripheral wall is in said second position and for sealing said passage means when said peripheral wall is in said first position.

11. The device of claim 10, wherein said means in said peripheral wall comprises a slit which is closed when said peripheral wall is in said first position and open when said peripheral wall is in said second position.

12. The device of claim 9, wherein said tubular member is axially divided into a pair of separable segments.

13. The device of claim 9, further comprising:

means in said passge means for operatively connecting said passage means to a cannula, when said second terminus is unsealed.

14. A device for providing access to a blood vessel of a living organism through the skin of said organism, comprising:

a housing adapted for implantation in said organism through an incision in the skin and subcutaneous tissue of said organism;

first means on said housing for (a) supporting said housing in said subcutaneous tissue, and (b) providing a sealing connection between said housing and the area of skin around said incision;

second means on said housing for encompassing and engaging the exterior surface of a selected blood vessel of said organism along a predetermined length of said blood vessel;

third means, mounted in said housing, for providing a fluid passage from the interior of said blood vessel, through an aperture in the wall of said blood vessel, to the surface of said skin;

fourth means operatively connected to said third means, and adapted for axial movement between a first position and a second position with respect to the interface between said passage and said aperture; and fifth means integral with said fourth means, for allowing fluid communication between the interior of said blood vessel and said passage, through said aperture when said fourth means is in said second position, and for sealing the interface between said passage and said aperture when said fourth means is in said first position.

15. The device of claim 14, wherein said third means has first and second ends, said passage extending between said first and second ends, said fourth means being mounted in said first end, and further comprising:

sixth means for selectably sealing said passage at said second end of said third means.

16. The device of claims 14 or 15, further comprising:

connection means in said third means for operatively connecting said third means to a cannula.

17. The device of claim 16 including said cannula and said cannula comprises:

a shaft having a fluid passage therethrough;

means on said shaft for operative connection to said connection means; and actuation means in said shaft for selectably moving said fourth means from said first position to said second position.

18. The device of claim 17, wherein said fourth means includes a resilient member, and said actuation means is adapted for selectively (a) moving said fourth means from said first position to said second position by distension of said resilient member, and (b) allowing the resilient return of said fourth means from said second position to said first position.

19. The device of claim 18 wherein said cannula further comprises:

means for selectively locking said actuation means to said shaft in a position in which said actuation means has moved said fourth means to said second position.

20. The device of claim 14 wherein said first means comprises:

a substantially open-sided substantially frustoconical structure for forming and receiving a substantially frustoconical tuck of skin from said area of skin around said incision; and a substantially frustoconical sealing member having a peripheral edge adapted for effecting a sealing contact against said tuck of skin and maintaining said tuck of skin in said structure.

21. A device for providing access to a blood vessel of a living organism through the skin and subcutaneous tissue of said organism, comprising:

a housing adapted for implantation in said organism through an incision in said skin and said subcutaneous tissue;

first means, mounted in said housing so as to be axially movable therein, for providing a fluid passage from the interior of said blood vessel, through an aperture in the wall of said blood vessel, through said subcutaneous tissue and said skin, said passage having a first terminus adapted for insertion into said aperture and a second terminus adapted for protrusion through said incision;

second means connected to said first means proximate said first terminus, for securing said first means to said blood vessel by engagement with the interior surface of said blood vessel;

third means on said housing, for forming and receiving a tuck of skin from the area around said incision;

fourth means engageable with said first means and said tuck of skin for securing said tuck of skin in said third means whereby the engagement between said fourth means and first means produces an axial movement of said first means in said housing, which movement strengthens the engagement between said second means and said interior surface of said blood vessel;

valving means in said passage and adapted for axial movement between a first position which seals said passage and a second position which allows fluid communication between said passage and the interior of said blood vessel when said first terminus is inserted into said aperture;

fifth means on said housing for encompassing and engaging the exterior surface of said blood vessel; and sixth means for selectively sealing said passage.

* * * * *

UNITED STATES PATENT AND TRADEMARK OFFICE
CERTIFICATE OF CORRECTION

PATENT NO. : 4,425,119

DATED : Jan. 10, 1984

INVENTOR(S) : Rickey T. Berglund

It is certified that error appears in the above-identified patent and that said Letters Patent is hereby corrected as shown below:

The title page should be cancelled to appear as per attached sheet. Cancel the Figs. of drawing 1-4 and substitute the attached Figs. 1-8.

United States Patent [19]

Berglund

[11] 4,425,119
[45] Jan. 10, 1984

[54] IMPLANTABLE DEVICE FOR INTRAVASCULAR ACCESS

[76] Inventor: Rickey T. Berglund, 2275-68 Caminito Pescado, San Diego, Calif. 92107

[21] Appl. No.: 342,113

[22] Filed: Jan. 25, 1982

[51] Int. Cl.³ ............................................. A61M 5/00
[52] U.S. Cl. .................................... 604/175; 128/1 R
[58] Field of Search ............ 604/4, 27, 29, 30, 32-34, 604/43, 52, 53, 93, 167, 169, 175, 178, 237, 284, 891, 896; 128/1 R; 3/1

[56] References Cited

U.S. PATENT DOCUMENTS

| | | | |
|---|---|---|---|
| 2,065,779 | 12/1936 | Williams | 604/178 |
| 3,461,869 | 8/1969 | Hargest | 604/175 |
| 3,540,451 | 11/1970 | Zeman | 604/175 X |
| 3,663,965 | 5/1972 | Lee, Jr. et al. | 604/175 X |
| 3,765,032 | 10/1973 | Palma | 604/175 X |
| 3,783,868 | 1/1974 | Bokros | 604/891 |
| 3,919,724 | 11/1975 | Sanders et al. | 604/175 X |
| 3,991,756 | 11/1976 | Synder | 604/175 X |
| 4,015,601 | 4/1977 | Bokros et al. | 604/175 |
| 4,016,884 | 4/1977 | Kwan-Gett | 604/175 |
| 4,069,826 | 1/1978 | Sessions et al. | 604/178 |
| 4,084,606 | 4/1978 | Mittleman | 604/30 X |
| 4,092,983 | 6/1978 | Slivenko | 604/175 |
| 4,106,491 | 8/1978 | Guerra | 604/167 |
| 4,108,173 | 8/1978 | Slivenko et al. | 604/175 |
| 4,108,174 | 8/1978 | Slivenko | 604/175 |
| 4,164,221 | 8/1979 | Bentley et al. | 604/52 |
| 4,183,357 | 1/1980 | Bentley et al. | 604/175 |
| 4,248,224 | 2/1981 | Jones | 604/53 |
| 4,306,545 | 12/1981 | Ivan et al. | 604/175 X |
| 4,318,401 | 3/1982 | Zimmerman | 604/53 X |
| 4,321,914 | 3/1982 | Begovac et al. | 604/896 X |
| 4,349,021 | 9/1982 | Raible | 604/175 |
| 4,350,157 | 9/1982 | Hoffa | 128/1 R X |

Primary Examiner—C. Fred Rosenbaum
Assistant Examiner—Michelle N. Lester
Attorney, Agent, or Firm—Gordon L. Peterson

[57] ABSTRACT

An implantable device for providing extracorporeal access to a blood vessel includes a core section having an axial passage for communication between the blood vessel and the exterior of an organism's skin. The core section is seated within a housing having a lower portion in the form of a tubular band which encompasses the blood vessel. The upper part of the housing has a circular rim supported by spaced-apart struts, forming an open-sided, bowl-like structure, through the center of which the upper portion of the core protrudes. The bowl-like structure allows the incised edges of the skin around the access site to be tucked into its interior. A sealing member is threaded onto the protruding section of the core and is configured to hold the skin so that the subcutaneous tissue can grow between the struts and reattach itself to the skin, thereby resulting in a permanent and stable implant. The interface between the core passage and the blood vessel is sealed by a resilient valving member which has a peripheral wall with one or more slits. The valve is opened by axial distension, so that the slits are opened to provide ports in communication with the interior of the blood vessel. To actuate the valve, a cannula having a movable rod is inserted into the passage, and the rod is urged downwardly so that its tip axially distends the valving member.

21 Claims, 8 Drawing Figures

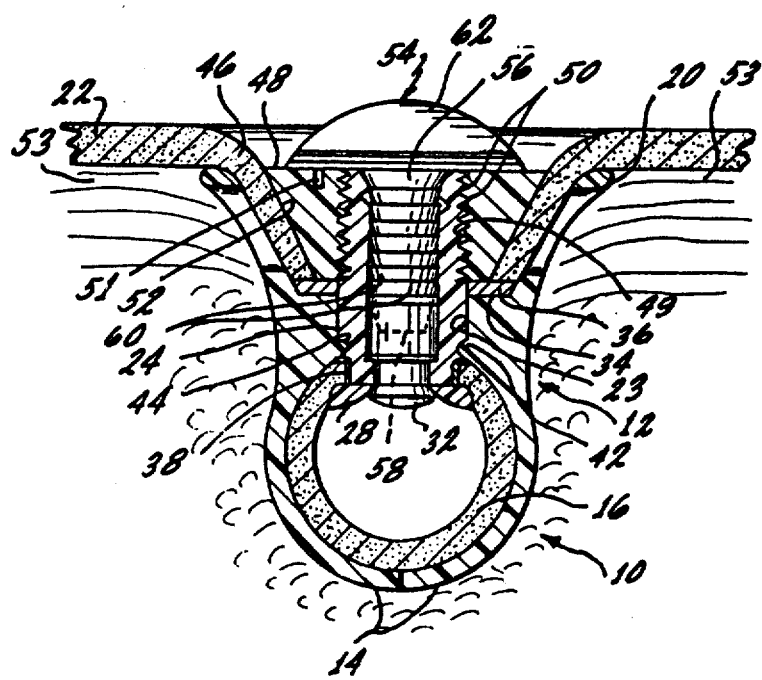

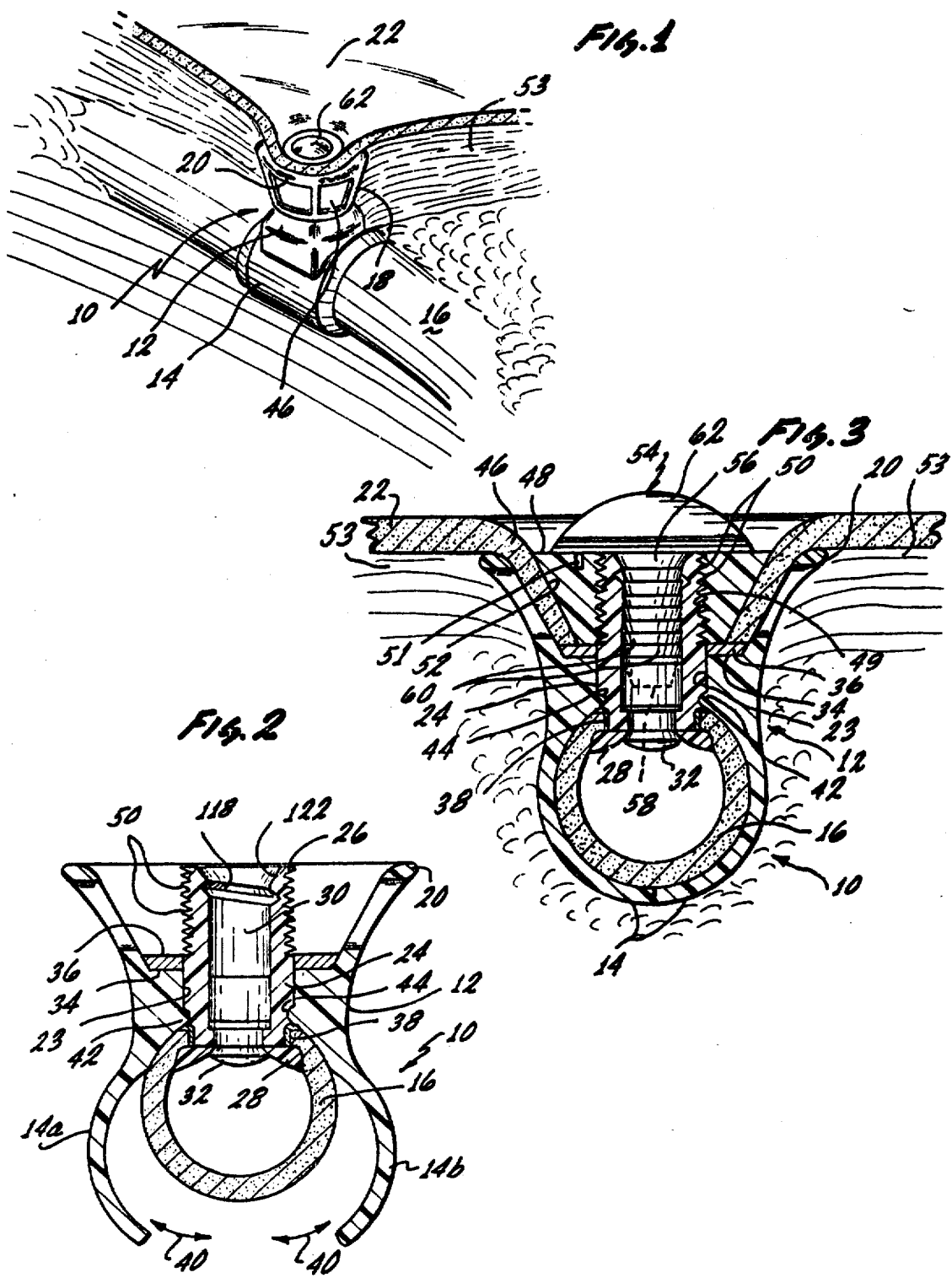

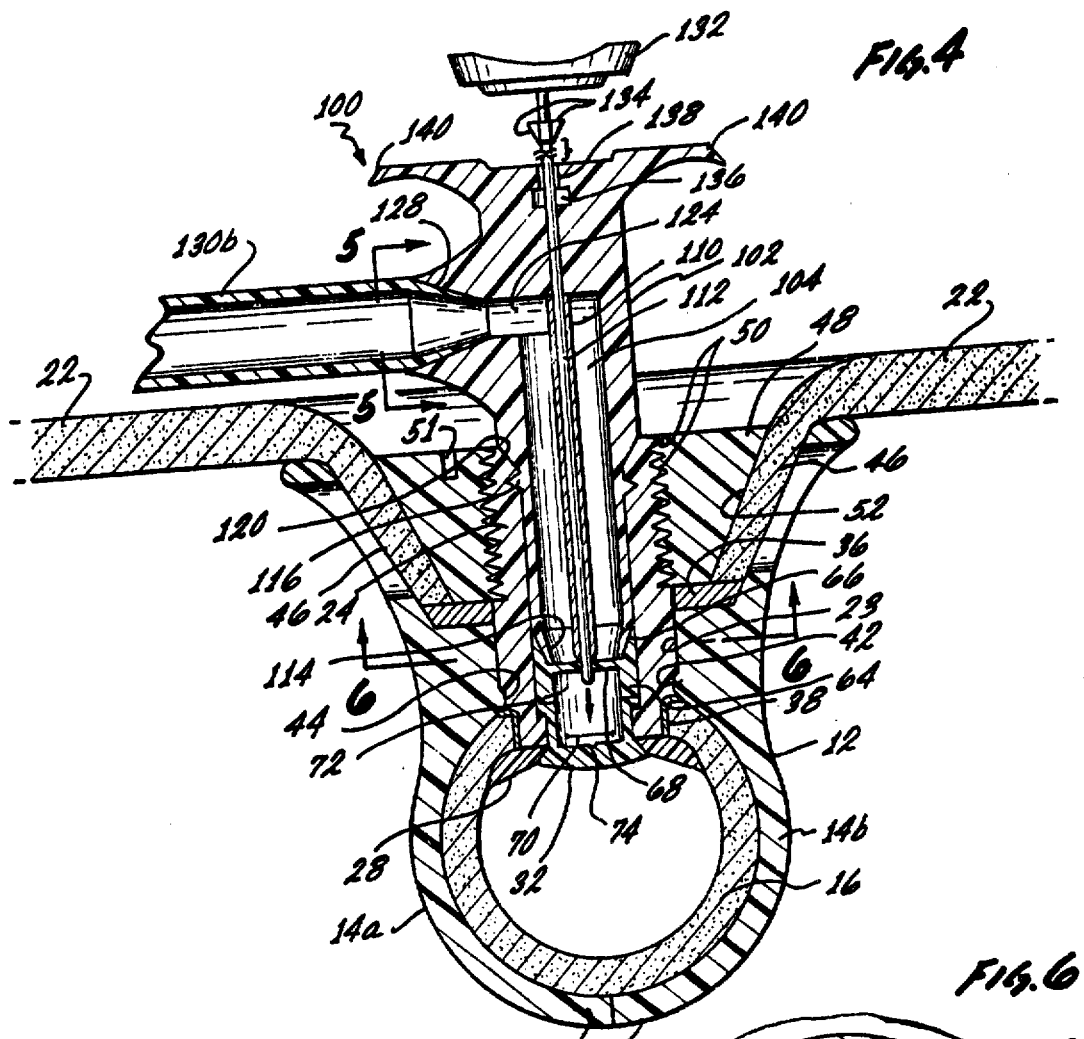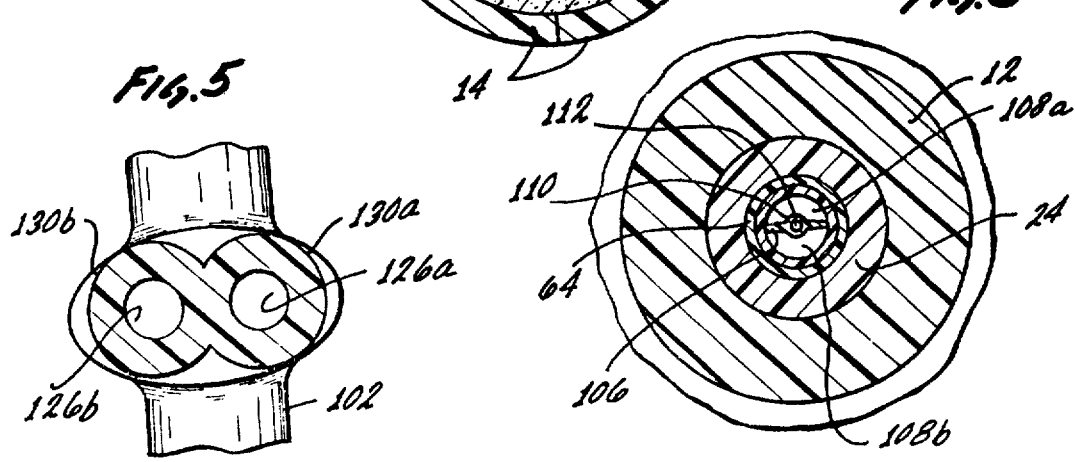

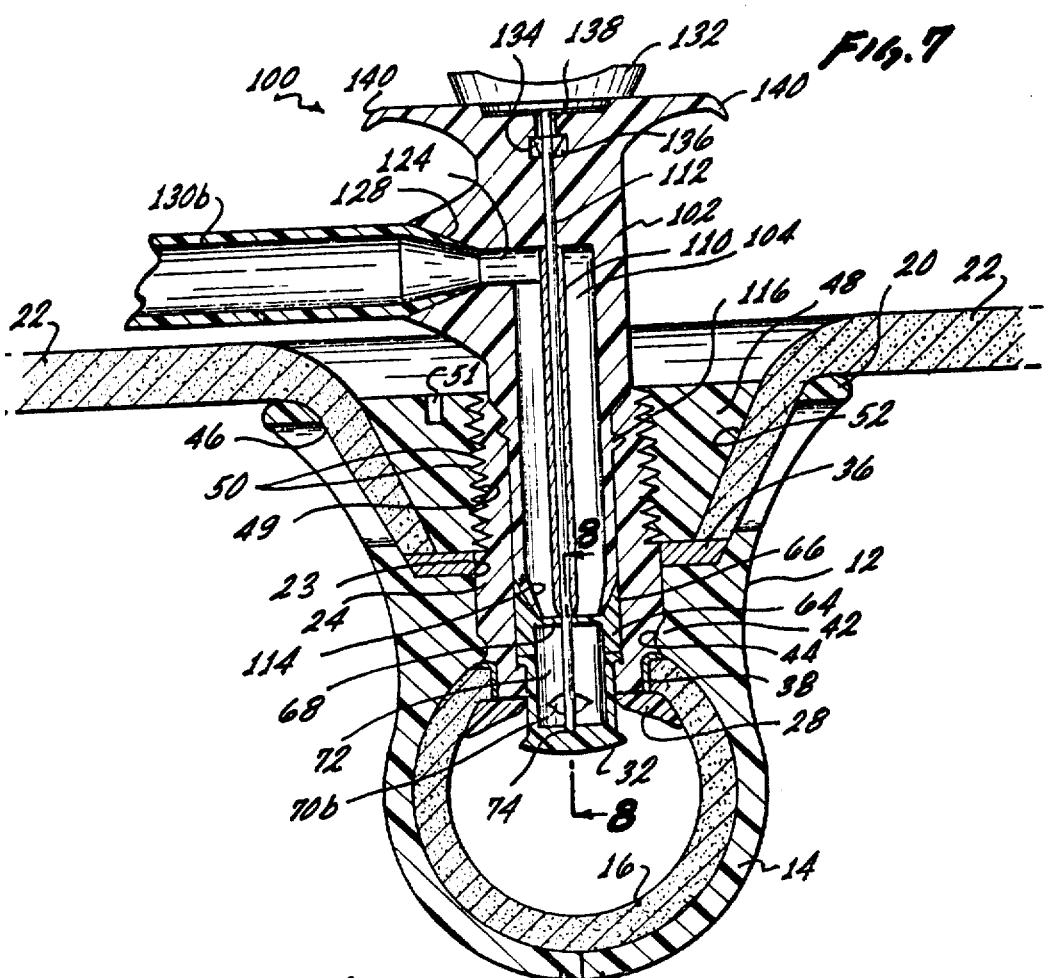
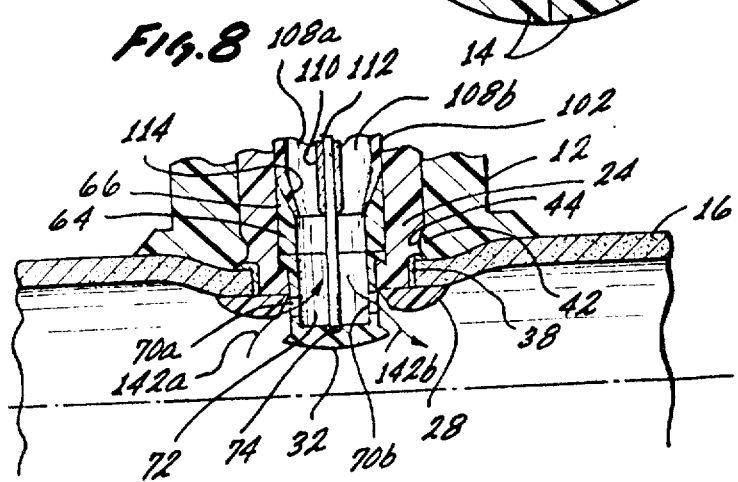

UNITED STATES PATENT AND TRADEMARK OFFICE
CERTIFICATE OF CORRECTION

PATENT NO. : 4,425,119
DATED : Jan. 10, 1984
INVENTOR(S) : Rickey T. Berglund

It is certified that error appears in the above—identified patent and that said Letters Patent is hereby corrected as shown below:

Col. 5, line 58 - change "comes" to -- come --

Col. 7, line 40 - change "defines" to -- define --

Col. 10, line 8 - change "sid" to -- said --

Col. 10, line 50 - change "prmot-" to -- promot- --

Col. 11, line 11 - change "lead" to -- load --

Col. 11, line 14 - change "claim 11" to -- claim 9 --

Signed and Sealed this

Eleventh Day of September 1984

[SEAL]

Attest:

GERALD J. MOSSINGHOFF

Attesting Officer

Commissioner of Patents and Trademarks